US007901681B2

(12) United States Patent
Stiles et al.

(10) Patent No.: US 7,901,681 B2
(45) Date of Patent: Mar. 8, 2011

(54) TRYPANOSOME DERIVED APOPTOTIC FACTORS (TAF)

(75) Inventors: Jonathan K. Stiles, Powder Springs, GA (US); Vincent C. Bond, Stone Mountain, GA (US); Michael Powell, Douglasville, GA (US)

(73) Assignee: Morehouse School of Medicine, Atlanta, GA (US)

( * ) Notice: Subject to any disclaimer, the term of this patent is extended or adjusted under 35 U.S.C. 154(b) by 676 days.

(21) Appl. No.: 10/871,354

(22) Filed: Jun. 18, 2004

(65) Prior Publication Data

US 2005/0281827 A1 Dec. 22, 2005

Related U.S. Application Data

(60) Provisional application No. 60/479,885, filed on Jun. 20, 2003.

(51) Int. Cl.
*A61K 39/00* (2006.01)
*A61K 39/38* (2006.01)
*A61K 39/395* (2006.01)

(52) U.S. Cl. .................. 424/139.1; 424/130; 424/131.1; 424/184.1; 424/269.1

(58) Field of Classification Search ........................ None
See application file for complete search history.

(56) References Cited

U.S. PATENT DOCUMENTS 6,955,810 B2 * 10/2005 Gotwals et al. ............ 424/144.1
2002/0082227 A1 6/2002 Henry

OTHER PUBLICATIONS

Barrett et al. The Lancet 2003 vol. 362: 1469-1480.*
Acosta-Serrano et al. PNAS. Feb. 2001 vol. 98 p. 1513-1518.*
Stebeck et al. Experimental Parasitology vol. 78 p. 432-436 1994.*
Roditi et al Molecular and Biochemical Parasitology vol. 91:117-130, Mar. 1998.*
Vassella et al, J. Mol. Biol. 312:597-607, 2001.*
Tian et al. Immunology Letters 75:161-162, 2001.*
Bilsborough et al. Acta Tropica 65:59-80, May 1997vassela.*
NCBI sequence database: accession No. AAK62893 (two pages).*
Stiles et al. Molecular and Biochemical Parasitology 133 ( Feb. 2004) 229-240.*
See Krammer et al (Nature vol. 407, No. 6805, p. 789-795, 2000).*
Savill et al (Nature vol. 407, No. 6805, p. 796-801, 2000).*
Stiles et al (Annals of Tropical Medicine and Parasitilogy, vol. 95, No. 8, 797-810, 2001).*
Xiao et al Cancer Research 63, 6825-6837, Oct. 15, 2003.*
Yang et al. Carcinogenesis, vol. 19, 611-616, 1998.*
International Search Report, International Preliminary Report on Patentability and the Written Opinion of the International Search Authority for PCT/US2005/019602, 2005.
Maranon et al., "HSP70 from *Trypanosoma cruzi* is Endowed with Specific Cell Proliferation Potential Leading to Apoptosis", International Immunology, vol. 12, No. 12, pp. 1685-1693, 2000.
Girard et al., "Cross-reactivity of Anti-galactocerebroside Autoantibodies with a *Trypanosoma brucei* Proteolipidic Epitope", Clin. Exp. Immunol., vol. 119m pp. 516-522, 2000.

* cited by examiner

*Primary Examiner* — N. M. Minnifield
*Assistant Examiner* — Oluwatosin Ogunbiyi
(74) *Attorney, Agent, or Firm* — Ping Wang; Andrews Kurth, LLP

(57) ABSTRACT

An antibody was raised against a synthetic 27 per peptide (ProEP2-1) blocked *T. brucei* and ProEP2-1-induced apoptosis in human brain vascular endothelial cells (HBVEC). The use of this and similar blocking antibodies have use both as diagnostic agents and in treatment to prevent damage arising from infection.

4 Claims, No Drawings

```
                         SEQUENCE LISTING

<160> NUMBER OF SEQ ID NOS: 1

<210> SEQ ID NO 1
<211> LENGTH: 27
<212> TYPE: PRT
<213> ORGANISM: Trypanosoma brucei

<400> SEQUENCE: 1

Ala Glu Gly Pro Glu Asp Lys Gly Leu Thr Lys Gly Gly Lys Gly Lys
1               5                   10                  15

Gly Glu Lys Glu Thr Lys Val Gln Asp Glu Val
            20                  25
```

TRYPANOSOME DERIVED APOPTOTIC FACTORS (TAF)

This application takes priority from U.S. provisional application 60/479,885 which was filed on Jun. 20, 2003.

FIELD AND BACKGROUND OF THE INVENTION

This invention relates to the use of anti-TAF monoclonal antibody to inhibit Trypanosoma-induced apoptosis of microvascular endothelial brain cells and other target cells.

Human African Trypanosomiasis (HAT, sleeping sickness) is a vector-borne parasitic disease. The parasite (Trypanosoma) is injected into the blood stream via the bite of blood-feeding tsetse flies (Glossina species) and maintains an extracellular existence. The parasites invade the central nervous system via the cerebrospinal fluid and cause apoptosis in brain cells leading to mental deterioration, coma and death. Other deleterious manifestations include meningo-encephalitis, neuronal demyelination and apoptosis, blood-brain barrier dysfunction, perivascular infiltration, astrocytosis and, among children who have been treated and cured of the infection, psychomotor and neurological retardation. Countries of tropical Africa, including Benin, Burundi, Burkina Faso, Cameroon, Democratic Republic of Congo, Cote d'Ivoire, Ethiopia, The Gambia, Ghana, Kenya, Liberia, Malawi, Mali, Mozambique, Nigeria, Niger, Rwanda, Senegal, Sudan, Togo, Uganda, Tanzania and Zimbabwe, are all countries with populations suffering from this disease. The use of therapies that would counter the pathologies resulting from this disease would greatly benefit the populations of this region.

It has previously been reported that HAT and other parasitic diseases such as cerebral malaria (the causative agent: Plasmodium falciparum) toxoplasmosis (caused by Toxoplasma gondii), Leishmaniasis (causative agent: Leishmania species) and Chagas disease (T. cruzi as causative agent) result in various apoptosis-mediated pathologies in host organs, including the brain. Human and mouse postmortem immunohistological analysis indicates that HAT causes structural damage to neurons, destroys cells lining the ventricles of the brain and damages brain macrovascular endothelial cells. Interestingly, T cruzi, Toxoplasma, Plasmodium and Leishmania inhibit apoptosis in host macrophages to enhance their proliferation. Although the molecular basis for the pathologies is not clearly understood, previous studies in this laboratory have shown that trypanosome infection resulted in extensive apoptosis at peak parasitaemia in the cerebellum of infected mice.

An initial search of the Entrez protein database revealed that TAF may be a procyclin-like precursor in Trypanosomo brucei stages. Furthermore, database searches on the National Center for Bioinformatics (NCBI) data base for trypanosome proteins identified trypanosome apoptotic factor (TAF) to be procyclin-like and was most likely one of the procyclins or was a procyclin derivative.

SUMMARY OF THE INVENTION

It is the purpose of this invention to provide antibodies which inhibit TAF-induced apoptosis. It was a particular object of the invention to provide mAb's that would bind the TAF or would neutralize or abrogate TAF activity. An antibody raised against a synthetic 27 per peptide (ProEP2-1) blocked T. brucei and ProEP2-1-induced apoptosis in human brain vascular endothelial cells (HBVEC). The use of this and similar blocking antibodies have use both as diagnostic agents in identifying presence of T. brucei and/or the peptide known to be a causative agent of apoptosis and in treatment to prevent damage arising from infection. This involves countering the pathology from infection with Trypanosoma species comprising administration of a trypanosome apoptotic-inhibiting effective amount of an antibody which inhibits pathological effects the trypanosome apoptotic factor in a carrier to an individual who has been exposed to infection with Trypanosoma species. The antibodies are given as composition of matter in a pharmaceutically acceptable carrier.

DETAILED DESCRIPTION OF THE INVENTION

A procyclin-like molecule has now been found to mediate apoptosis arising from infection with Trypanosoma. The trypanosome apoptotic factor (TAF) is an 8.5 kDa heal-labile, proteinase-K degradable factor present in Trypanosoma brucei and is associated with apoptosis in cerebellar and brain stem macrovascular endothelium of trypanosome-infected mice and in human HBVEC. That protein is effectively blocked by antibodies against that protein. A monoclonal antibody (mAb) was raised against a synthetic protein (ProEP2-1) of the formula AEGPEDKGLTKG-GKGKGEKETI(VQEV AEGPEDKGLTKG-GKGKGEKETKVQDEV (SEQ ID No. 1) (AF353627) corresponding to a region common to EP procyclin (EP2-1). The ProEP2-1 was found to induce apoptosis in HBVEC and in cerebella of mice similar to that induced by T. brucei. Western blot analysis utilizing the anti-procyclin monoclonal antibody (mAB) revealed that TAF is present in infected brain tissue lysates, but not in uninfected lysates. TAF-induced apoptosis in HBVEC was blocked by the mAb. Furthermore, that same mAb blocked T. brucei- and ProEP2-1-induced apoptosis in HBVEC in vitro. The discovery provides a novel alternative for protecting against trypanosome-induced pathologies. Blocking TAF or TAF-regulated mechanisms in vivo, can eliminate or effectively reduce trypanosome-induced apoptosis. Similar TAF derivatives or derivatives of other TAF-like parasite-derived apoptotic agents from species of Trypanosoma can also be used to block apoptotic effects of those infections. The methods of the invention also have application for use against infectious agents and the apoptotic effects caused by them, particularly infection cause by trypanosome-like organisms.

While the preferred embodiment of the instant invention is use of monoclonal antibodies disclosed herein which inhibit activity of the pathology-causing fragment, antigen-binding antibodies may also be isolated from the serum of immunized mammalian hosts, immortalized cell lines, lymphoblastoids or by known methods of recombinant biology. The antibodies may be linked to markers such as fluorescein dyes or radioactive tags. Obviously other mAb's against TAF can by developed. Compositions containing apoptosis inhibiting-effective amounts of antibodies that block TAF can be delivered systemically in the commonly used carriers such as normal saline, half-normal saline, 10% glucose in saline, Ringer's solution, etc. The antibodies may be administered subcutaneously, intravenously, intramuscularly or, in a preferred embodiment, intrathecally. The intrathecal administration may be particularly effective and would require smaller amounts of the medication. Intravenous administration using a carrier such as DMSO would facilitate transfer across the blood-brain barrier. The antibodies of the invention can also be conjugated to other molecules which may act as targetting or carrier molecules such as peptides, proteins, nucleic acid sequences or carbohydrates. It is understood, of course, that the methods of the invention can be used in any animal form that suffers from infection with *Trypanosoma* organisms.

For diagnostic purposes relating to CNS infections, antibodies, including, as a preferred embodiment, the mAb exemplified herein may be used. Tagged antibodies can be used to identify the protein in cerebrospinal fluid or serum samples obtained from patients suspected of having HAT. Modified TAF or fragments therefrom could also be used as a vaccine to protect against TAF-induced pathologies. Such antigenic peptides and proteins could be administered with adjuvants appropriate for the means of administration. For example, they may be administered intranasally in liquid or particulate form in sprays. In many instances it may be appropriate to administer the vaccines in the form of microspheres. Adjuvants would include chemokines, Fruend's adjuvant, etc. The antibodies against the ProEP2-1 can be used to isolate and characterize TAF and to identify TAF on mammalian host cells, thus providing means for evaluating presence of TAF in. mammalian sera or cerebrospinal fluid, thus providing means for evaluating presence of TAF in vivo and in vitro.

The use of TAF as a means of evaluating therapeutic agents for treatment of apoptotic responses to infectious diseases is also an aspect of this invention. See, particularly, example 1 below. In particular, the invention envisions evaluating agents for possible benefit in treatment of human African trypanosomiasis by administration of an apoptosis-causing effective amount of trypanosome apoptotic factor concurrent with or followed by administration of the agent being tested, to a mammal susceptible to thrypanosomiasis, then evaluating the disease process in the mammals who are being studied.

Materials and Methods

EXAMPLE 1

Murine African trypanosomiasis model. All animal-related procedures were carried out in strict accordance with the *National Institutes of Health Guide for the Care and Use of Laboratory Animals* and approved by the Morehouse School of Medicine's Animal Care and Use Committee. Male Balb/c mice (6-8 weeks of age) were maintained on a 12-hour-light/12-hour-dark cycle with access to food and water ad libitum. Mice were injected intra-peritoneally with parasitized blood (*T. brucei* L427) and groups of 10 were then sacrificed on days 0, 4, 6 and 8 post-infection (P.I.). Equal numbers of mice were sham-injected (with uninfected blood) as controls. All experiments were repeated twice at different times to ensure that the data were representative of each group, and took into account the potential individual-host variation in trypanosome-induced global gene expression. This murine trypanosomiasis model mimics the major clinical symptoms of HAT, with the infected mice developing fever, tremors, lethargy, weight loss, dyskinesia, convulsions, altered gait, and death by day 10 post injection (P.I.).

Cultivation of Trypanosoma brucei in vitro. Trypanosoma brucei culture blood stages (BF) were cultivated at 37° C. in HMI-9 medium, based on Iscove's modification (IMDM) of Dulbecco's MEM (Modified Eagles Medium)that is now most widely used for culture adapted BF *T. brucei*. Procyclic cultures were grown at 28° C. in Cunningham's medium supplemented with 15% (v/v) heat inactivated fetal calf serum. Adapted procyclic cultures mimic insect gut parasite forms and have been shown to undergo cyclical development in tsetse flies. These stages express an abundant glycoprotein, a procyclin, which is upregulated in parasites in the gut of the tsetsefly vector. For the purposes of generating abundant amounts of procyclin for. apoptotic assays, procyclic forms were cultured as described above instead in blood stages.

Mouse cerebellum and apoptosis analysis. Neuronal apoptosis in the brains of infected and uninfected mice as well as mice injected with equivalent amounts of parasite-free supernates (TAF) of cultured procyclics or synthetic peptides were investigated and was confirmed by TdT-mediated dUTP-digoxigenin nick end labelling (TUNEL) of apoptotic cells, using a commercial kit (Apoptag; Oncor, Beverly, Mass.) according to the manufacturer's instructions. The level of apoptosis visible in brain sections was determined semi-quantitatively as the mean numbers of TUNEL-positive (i.e. apoptotic) cells/$cm^2$ in 20 comparative fields of brain sections from infected and uninfected mice.

RBVEC Cell line: Human Brain Macrovascular Endothelial Cells (HBVEC) were obtained from Biowhittaker (Walkersville, Md.). They were grown in media made as per the instructions in the Complete Medium Kit (Cell Systems Corporation, Kirkland, Wash.). Briefly, 500 ml of Complete Medium was added to 10 ml of Attachment Factor (Cell Systems Corporation, Kirkland, Wash.). The medium is a liquid medium containing 10% serum and CSC Growth factor. Cell stocks were maintained in T25 flasks at 37° C. in a 5% CO2 incubator, and were harvested and passed at about 60-80% confluence. Experiments were performed on cells plated and grown for 24 to 48 hours on collagen-coated coverslips in 35 mm tissue culture dishes.

Terminal deoxynucleotidyl transferase dUTP nick-end labeling (TUNEL) assay. Apoptosis generates in free DNA ends which can be labeled in situ using terminal deoxynucleotidyl-transferase (TdT), incorporating an exogenously added labeled nucleotide into the DNA strand. This label can then be visualized directly by fluorescence, or indirectly using anti-FITC-peroxidase, and a colorimetric assay. Cells on cover slips were washed with PBS, and fixed for 30 minutes at RT with 4% paraformaldehyde, in PBS, pH 7.4. They were then washed with PBS, and permeabilized with 0.1% TRITON X-100™ for 10 minutes at room temperature (RT). The slides were rinsed twice with PBS, and air-dried for 2 minutes. Then the manufacturer's procedure for TUNEL staining the slides was followed exactly (manufacturer's procedure for the In Situ Cell Death Detection Kit, AP; Boehringer Mannheim, Indianapolis, Ind.). Total cell counts were determined by counterstaining fixed cultures with 20:g/ml of Hoechst 33258. All specimens were observed by epifluorescence on a computer-controlled microscope system based on a Zeiss Axioskop microscope (Carl Zeiss, Thornwood, N.Y.), and the images were acquired and examined using a charged coupled device (CCD) camera, MAGNAFIRE™, model S99806 (Olympus American, Melville, N.Y.). Images were examined using Image-Pro Plus 4.1 for Windows (Media Cybernetics, Silver Springs, Md.) software.

EXAMPLE 2

Dose Response. The effect of Trypanosome conditioned serum containing medium-induced apoptosis was determined in HBVEC. Cells were grown on coverslips, and either treated with unconditioned Trypanosome medium or treated with various concentrations of Trypanosome conditioned serum containing medium or synthetic 27 mer peptide (ProEP2-1) for 24 hours. Subsequently, the cultures were assayed for apoptosis by the TUNEL assay. Total cells, and fluorescent cells were counted for each field examined (10 fields per plate minimum). The percentage of TUNEL-labeled cells was calculated as the number of FITC-stained cells divided by the total number.of cells. The data from at least three independent experiments were collated, standard errors of measurement were calculated, and these data are shown plotted against the concentration of Trypanosome conditioned serum containing medium per ml of HBVEC growth medium Characterization of TAF by SELDI mass spectrometry. Surface Enhanced Laser Desorption Ionization (SELDI) is a mass spectrometry technique that combines different reactive surfaces known as Protein Chips with detection by mass spectrometry. The chips come in a variety of different surfaces each with a different reactive chemistry that allows partial purification of complex mixtures of proteins prior to detection. Currently available surfaces in use include anion exchange, cation exchange, hydrophobic, metal chelate, and activated surfaces. The activated surfaces allow for the covalent attachment of proteins to make custom affinity chips. After the partial purification on the chip detection and molecular weight determination can be rapidly determined by the mass spectrometer. In this study this technology was used to determine the molecular weight of TAF.

ProteinChip Analysis. Two microliters of processed culture supernatant containing the TAF was added to a gold surface SELDI chip. One microliter of sinapinic acid, prepared according to the manufacturer's instructions (Ciphergen Biosystems, Fremont, Calif.) was then mixed with the sample and the mixture was allowed to air dry. The chip was then analyzed on a PBS-II mass reader (Ciphergen) using SELDI 2. lb software (Ciphergen) calibrated with vaspressin (1084.24 Da), somatostatin (1637.90 Da), bovine insulin $-chain (3495.94 Da), human insulin (5807.65 Da), and Hirudin BHVK (7033.61 Da). Data were collected by averaging 100 laser shots with an intensity of 240 and a detector sensitivity of 10.

EXAMPLE 3

Antibody blocking assay. To confirm that TAF was a procyclin or derivative thereof, the apoptosis activity of TAF was blocked using anti-procyclin monoclonal antibody (CLPOOlA, Cedarlane, Ontario, Canada). This antibody was also used to block apoptosis activity induced in HBVEC by our synthetic 27 mer peptide (ProEP2-1, AEGPEDKGLT-KGGKGKGEKETKVQDEV) (Seq. ID No. 1)) corresponding to a region common to EP procyclin (EP2-1). Briefly, anti-procyclin mAb was diluted (1:250-1:500) into a 50 μL aliquot of either trypanosome conditioned medium, or trypanosome free medium. This solution was allowed to sit for 1 hour at RT. Then each solution was diluted into 1 ml of HBVEC culturing medium and HBVEC cells on cover slips were treated with one of these solutions for 24 hours at 37 C.

Data Analysis. SigmaStat 2000 (Chicago, Ill.) software was used to analyze and confirm the statistical significance of data. The data were subsequently analyzed by the Student's t-test, using a two-factor, unpaired test. In this analysis, treated samples were compared to untreated controls. The significance level was set at $p<0.05$.

Results

Murine Trypanosomiasis Model All the mice inoculated with *T. brucei* exhibited lethargy, coma, abnormal movements (dyskinesia, convulsions) and altered gait at peak parasitaemia. Death occurred beyond 8 days p.i (data not shown), at peak parasitaemia. The fur of infected mice was abnormally thin by day 4 P.I. and abnormally thick by day 8. No alterations in coat condition or any clinical signs were observed in the sham-injected, uninfected mice.

Mouse cerebellum and apoptosis. TUNEL analysis on duplicate sections of T. brucei infected and uninfected as well as TAF injected mouse brain sections indicated extensive DNA fragmentation (>50% of cells apoptotic) in the cerebellum but significantly lower in other regions at peak parasitaemia. The cerebellums of uninfected controls showed the very small numbers of apoptotic cells (0%-3% of cells apoptotic) that are consistent with normal cell-cycle events.

Terminal deoxynucleotidyl transferase dUTP nick-end labeling (TUNEL) assay. TUNEL labeling of HBVEC due to trypanosome conditioned medium and later by synthetic 27 mer peptide (ProEP2-1, data not shown) was evaluated. TUNEL labeling exceeded 10% beyond 0.005:1/ml and an LD 50 at approximately 5.0:1/ml. Controls showed no change in percent labeling of cells. TUNEL labeling of HBVEC exposed to parasite-conditioned medium and synthetic 27 mer peptide (ProEP2-1) is dose dependent.

EXAMPLE 4

Heat and Protease Effects. Pretreating the trypanosome conditioned medium with either Heat or Protease protects exposed HBVECs from trypanosome-conditioned serum medium-induced apoptosis. HBVEC cultures were exposed to each of the following conditions: unconditioned trypanosome medium; unconditioned trypanosome medium kept on ice for 0.5 hr; with trypanosome conditioned medium kept on ice for 0.5 hr; trypanosome conditioned medium pretreated at 70° C. for 30 min; or trypanosome conditioned medium pretreated with protease inhibitor (Proteinase K, 51/ml, 37° C. for 30 min. Subsequently, the cultures were assayed for apoptosis by the TUNEL assay. Total cells, and fluorescent cells were counted for each field examined (10 fields per plate minimum). The percentage of TUNEL-labeled cells was calculated as the number of FITC-stained cells divided by the total number of cells. The data from at least three independent studies were collated, standard errors of measurement were calculated.

Serum effects in culture medium. The apoptotic effect on HBVEC of trypanosome conditioned serum-free medium was determined to differentiate serum effects from that of parasites. Serum components contributed about 5% of apoptotic effect. Serum-free medium induced significant apoptosis in HBVEC's. The apoptotic factor is parasite derived and highly potent. Cells were grown on cover slips, and either treated with unconditioned trypanosome medium, trypanosome-conditioned serum containing medium, or with trypanosome-conditioned serum-free medium for 24 hours. Subsequently, the cultures were assayed for apoptosis by the TUNEL assay. Total cell, and fluorescent cell counts were made for each field examined (10 fields per plate minimum). The percentage of TUNEL-labeled cells was calculated as the number of FITC-stained cells divided by the total number of cells. The data from at least three independent experiments were collated, standard errors of measurement were calculated, and these data are shown plotted against the treatment.

EXAMPLE 5

Antibody blocking assay. Specificity of trypanosome-conditioned serum containing medium-induced apoptotic effect on HBVEC was determine. Trypanosome conditioned medium was untreated or treated with anti-procyclin antibody for 1 hr at RT. Subsequently, HBVEC cultures were exposed to these solutions of conditioned medium as well as to ProEP2-1 for 24 hours, and then the cultures were assayed for apoptosis by the TUNEL assay. Total cells, and fluorescent cells were counted for each field examined (10/fields per plate minimum). The percentage of TUNEL-labeled cells was calculated as the number of FITC-stained cells divided by the total number of cells. The data from at least three independent experiments were collated, standard errors of measurement were calculated, and these data are shown plotted against the treatment. The treatments included: untreated HBVEC cultures; cultures exposed to normal medium/serum+anti-procyclin antibody at 1:250 dilution, or 1:500 dilution; cultures exposed to trypanosome conditioned serum free medium, plus anti-procyclin antibody at 1:250 dilution, or 1:500 dilution; and cultures exposed to trypanosome conditioned serum containing medium, plus anti-procyclin antibody at 1:250 dilution, or 1:500 dilution. TAF- and ProEP2-1-induced apoptosis in HBVEC were blocked by anti-procyclin antibody suggesting that anti-procyclin antibody may bind or neutralize TAF or TAF derivatives.

DNA Ladder. Neutral gel electrophoresis of extracted DNA from HBVEC cultures treated under various conditions. Apoptotic factor is present in trypanosome conditioned medium and absent in unconditioned trypanosome growth medium. Cells were either treated with unconditioned trypanosome growth medium (1:20 dilution), Trypanosome conditioned serum containing medium (1:20 dilution), or with 8 g/ml ceramide. Cultures were harvested for DNA, the resultant DNA electrophoresed and analyzed for DNA fragmentation. DNA size standards were DNA ladder markers (Promega, Madison, Wis.).

Protein chip assay Analysis of the SELDI spectrum revealed a single major peak at 8652.7. A search of the Entrez protein database was done using the terms "trypanosoma AND 008500:008700 [Molecular Weight]. The first protein listed in the search was EP2-1 procyclin precursor (*Trypanosoma brucei*). Since this protein is a surface protein it was selected for further evaluation. Further database searches on the National Center for Bioinformatics (NCBI) database for trypanosome proteins in this range identified the most likely candidate to be procyclin-like or procyclin EP2-1.

EXAMPLE 6

Dogs who have been exposed to TAF in the manner of Example 1 are treated 2 days P.I. with 1 ml of a 1:250 dilution of the mAb against the synthetic protein used in the antibody blocking assay using, as a carrier, 10% glucose in ½ normal saline injected intrathecally into the subdural space at in the lumbar region.

Since the Trypanosomes enter the CNS through the cerebral spinal fluid, the administration of antibodies which neutralize or bind the pathology-inducing component intrathecally is deemed especially beneficial.

A method of testing for diagnosing presence or absence of human African trypanosomiasis (HAT) by the methods exemplified in example 5 is also an important part of the invention. Following the steps of obtaining a sample of cerebral spinal fluid from the patient suspected of having HAT, contacting the fluid collected with a labelled antibody against trypanosome apoptotic factor, followed by examining the sample to determine whether the labelled antibody has bound to any cells found in the cerebral spinal fluid can provide a particularly sound method of evaluation, since the causative organism is known to enter the cerebral spinal fluid.

What we claims is:

1. A method for inhibiting the effects of trypanosome apoptotic factor in a patient suffering from *Trypanosoma brucei* induced apoptosis by the administration of an apoptotic inhibiting effective amount of an anti-procyclin antibody to SEQ ID NO: 1, the trypanosome apoptotic factor, said antibody being administered in a pharmaceutically acceptable carrier to said patient.

2. A method for inhibiting apoptotic damage to brain cells induced by trypanosome apoptotic factor comprising contacting said cells with a molecule that specifically binds to SEQ ID NO: 1, the trypanosome apoptotic factor, in an amount sufficient to inhibit apoptosis, wherein the molecule is an antibody.

3. The method of claim 1, wherein the antibody is administered intrathecally.

4. The method of claim 1, wherein the antibody is administered intramuscularly.

* * * * *